(12) United States Patent
Abe et al.

(10) Patent No.: US 11,241,206 B2
(45) Date of Patent: Feb. 8, 2022

(54) X-RAY IMAGING APPARATUS

(71) Applicant: CANON MEDICAL SYSTEMS CORPORATION, Otawara (JP)

(72) Inventors: Shingo Abe, Nasushiobara (JP); Akihito Takahashi, Nasushiobara (JP); Takayuki Ishikawa, Nasushiobara (JP); Mitsuru Sakata, Yaita (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 331 days.

(21) Appl. No.: 15/924,495

(22) Filed: Mar. 19, 2018

(65) Prior Publication Data
US 2018/0271464 A1 Sep. 27, 2018

(30) Foreign Application Priority Data

Mar. 21, 2017 (JP) .............................. JP2017-054139
Mar. 15, 2018 (JP) .............................. JP2018-048288

(51) Int. Cl.
*A61B 6/00* (2006.01)
*A61B 6/03* (2006.01)
(Continued)

(52) U.S. Cl.
CPC .............. *A61B 6/463* (2013.01); *A61B 6/032* (2013.01); *A61B 6/0407* (2013.01); *A61B 6/0487* (2020.08); *A61B 6/06* (2013.01); *A61B 6/40* (2013.01); *A61B 6/42* (2013.01); *A61B 6/4441* (2013.01); *A61B 6/461* (2013.01);
(Continued)

(58) Field of Classification Search
CPC ....... A61B 6/463; A61B 6/032; A61B 6/0407; A61B 6/0457; A61B 6/06; A61B 6/40; A61B 6/42; A61B 6/4441; A61B 6/461; A61B 6/467; A61B 6/487; A61B 6/54; A61B 6/542
See application file for complete search history.

(56) References Cited

U.S. PATENT DOCUMENTS 5,572,566 A * 11/1996 Suzuki ................... A61B 6/145
378/98.2
7,602,882 B2 * 10/2009 Dorre ..................... A61B 6/467
378/117

(Continued)

FOREIGN PATENT DOCUMENTS

| JP | 6-20486 | 6/1994 |
|----|---------|--------|
| JP | 2009-82468 | 4/2009 |
| JP | 2011-161211 | 8/2011 |

*Primary Examiner* — Blake C Riddick
(74) *Attorney, Agent, or Firm* — Oblon, McClelland, Maier & Neustadt, L.L.P.

(57) ABSTRACT

An X-ray imaging apparatus according to an embodiment includes an X-ray generator, an X-ray detector, an input interface, and processing circuitry. The processing circuitry is configured to: display, on a display, an image based on X-rays detected by the X-ray detector; control, based on a first control signal according to the direction signal, a rotating mechanism of the arm so that the arm performs a first rotation; and control, in response to an end of the first rotation, based on a second control signal, the rotating mechanism so that the arm performs a second rotation which returns the arm toward a position before the first rotation, the position being stored in a memory circuit.

16 Claims, 14 Drawing Sheets

(51) Int. Cl.
*A61B 6/04* (2006.01)
*A61B 6/06* (2006.01)

(52) U.S. Cl.
CPC .............. *A61B 6/467* (2013.01); *A61B 6/487* (2013.01); *A61B 6/54* (2013.01); *A61B 6/542* (2013.01)

(56) References Cited

U.S. PATENT DOCUMENTS

| | | | | |
|---|---|---|---|---|
| 2005/0117703 | A1* | 6/2005 | Oota | A61B 6/102 378/117 |
| 2009/0087068 | A1 | 4/2009 | Sakaguchi | |
| 2010/0166152 | A1* | 7/2010 | Takemoto | A61B 6/4476 378/197 |
| 2010/0215149 | A1* | 8/2010 | Takemoto | A61B 5/02007 378/98 |
| 2013/0322719 | A1* | 12/2013 | Dekel | A61B 6/583 382/131 |
| 2015/0063537 | A1* | 3/2015 | Lee | A61B 6/022 378/41 |
| 2015/0063541 | A1* | 3/2015 | Kobayashi | A61B 6/12 378/62 |
| 2015/0313564 | A1* | 11/2015 | Narabu | A61B 6/022 378/42 |
| 2015/0342548 | A1* | 12/2015 | Zaiki | A61B 6/467 378/41 |
| 2015/0351712 | A1* | 12/2015 | Ohishi | A61B 6/027 378/62 |
| 2016/0113604 | A1* | 4/2016 | Noshi | A61B 6/467 600/431 |

* cited by examiner

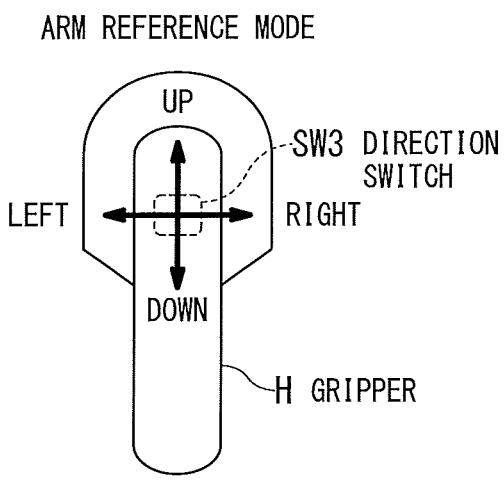
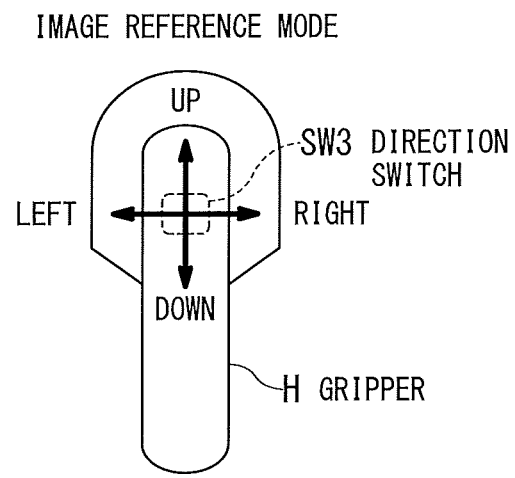
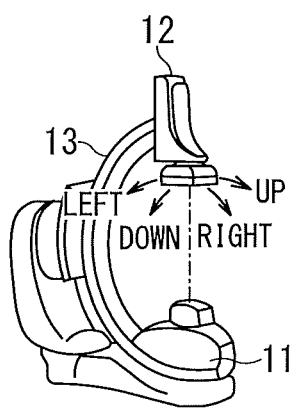
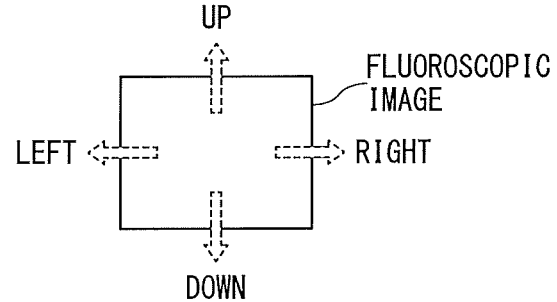
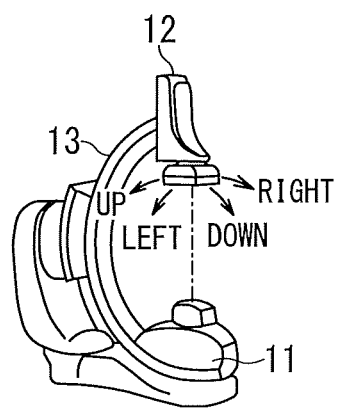
FIG. 7A          FIG. 7B

| DIRECTION SIGNAL | FIRST CONTROL SIGNAL | |
|---|---|---|
| | ARM REFERENCE MODE | IMAGE REFERENCE MODE |
| LEFT | CRA (VELOCITY 100%) | RAO (VELOCITY 100%) |
| RIGHT | CAU (VELOCITY 100%) | LAO (VELOCITY 100%) |
| UP | LAO (VELOCITY 100%) | CRA (VELOCITY 100%) |
| DOWN | RAO (VELOCITY 100%) | CAU (VELOCITY 100%) |
| UPPER LEFT 45-DEGREE | CRA (VELOCITY 50%) + LAO (VELOCITY 50%) | RAO (VELOCITY 50%) + CRA (VELOCITY 50%) |
| LOWER LEFT 45-DEGREE | CRA (VELOCITY 50%) + RAO (VELOCITY 50%) | RAO (VELOCITY 50%) + CAU (VELOCITY 50%) |
| UPPER RIGHT 45-DEGREE | CAU (VELOCITY 50%) + LAO (VELOCITY 50%) | LAO (VELOCITY 50%) + CRA (VELOCITY 50%) |
| LOWER RIGHT 45-DEGREE | CAU (VELOCITY 50%) + RAO (VELOCITY 50%) | LAO (VELOCITY 50%) + CAU (VELOCITY 50%) |

FIG. 8A

| DIRECTION SIGNAL | FIRST CONTROL SIGNAL | |
|---|---|---|
| | ARM REFERENCE MODE | IMAGE REFERENCE MODE |
| LEFT | CAU (VELOCITY 100%) | RAO (VELOCITY 100%) |
| RIGHT | CRA (VELOCITY 100%) | LAO (VELOCITY 100%) |
| UP | RAO (VELOCITY 100%) | CRA (VELOCITY 100%) |
| DOWN | LAO (VELOCITY 100%) | CAU (VELOCITY 100%) |
| UPPER LEFT 45-DEGREE | CAU (VELOCITY 50%) + RAO (VELOCITY 50%) | RAO (VELOCITY 50%) + CRA (VELOCITY 50%) |
| LOWER LEFT 45-DEGREE | CAU (VELOCITY 50%) + LAO (VELOCITY 50%) | RAO (VELOCITY 50%) + CAU (VELOCITY 50%) |
| UPPER RIGHT 45-DEGREE | CRA (VELOCITY 50%) + RAO (VELOCITY 50%) | LAO (VELOCITY 50%) + CRA (VELOCITY 50%) |
| LOWER RIGHT 45-DEGREE | CRA (VELOCITY 50%) + LAO (VELOCITY 50%) | LAO (VELOCITY 50%) + CAU (VELOCITY 50%) |

FIG. 8B

X-RAY IMAGING APPARATUS

CROSS-REFERENCE TO RELATED APPLICATION

This application is based upon and claims the benefit of priority from Japanese Patent Application No. 2017-054139, filed on Mar. 21, 2017, and Japanese Patent Application No. 2018-048288, filed on Mar. 15, 2018, the entire contents of each of which are incorporated herein by reference.

FIELD

An embodiment as an aspect of the present invention relates to an X-ray imaging apparatus.

BACKGROUND

In recent years, opportunities to perform surgery under X-ray fluoroscopy using an X-ray imaging apparatus have been increasing. The X-ray imaging apparatus can support the IVR (Interventional Radiology) surgery using the X-ray fluoroscopy. The IVR surgery using the X-ray fluoroscopy means mainly treatment using a catheter during the X-ray fluoroscopy. The X-ray imaging apparatus generates fluoroscopic images in chronological order and displays them in real time in IVR surgery using the X-ray fluoroscopy.

During the X-ray fluoroscopy, the X-ray imaging apparatus fixes a rotational position of a C-arm to a working angle and performs the X-ray fluoroscopy at the fixed angle to display the fluoroscopic images. However, each fluoroscopic image is a planar projected image. Therefore, it is difficult for an operator operating the catheter, to recognize a three-dimensional positional relationship even if viewing the fluoroscopic images. That is, it is difficult for the operator to recognize the positional relationship in the depth direction of the line of sight.

Thus, in the X-ray imaging apparatus, a situation often occurs during the X-ray fluoroscopy, in which a C-arm is rotated to change the rotational position and then fluoroscopic images with different angles are generated and displayed. By displaying the fluoroscopic images with different angles, the operator is able to easily recognize the degree of bending of the catheter on the images and the three-dimensional structure on the images.

On the other hand, rotation of the C-arm may be performed by an operation of the operator or by an assistant different from the operator. When the rotation operation of the C-arm is performed, the operator has to interrupt the surgical procedure using the catheter and then perform the rotational operation of the C-arm.

BRIEF DESCRIPTION OF THE DRAWINGS

In accompanying drawings.

Figure 2:
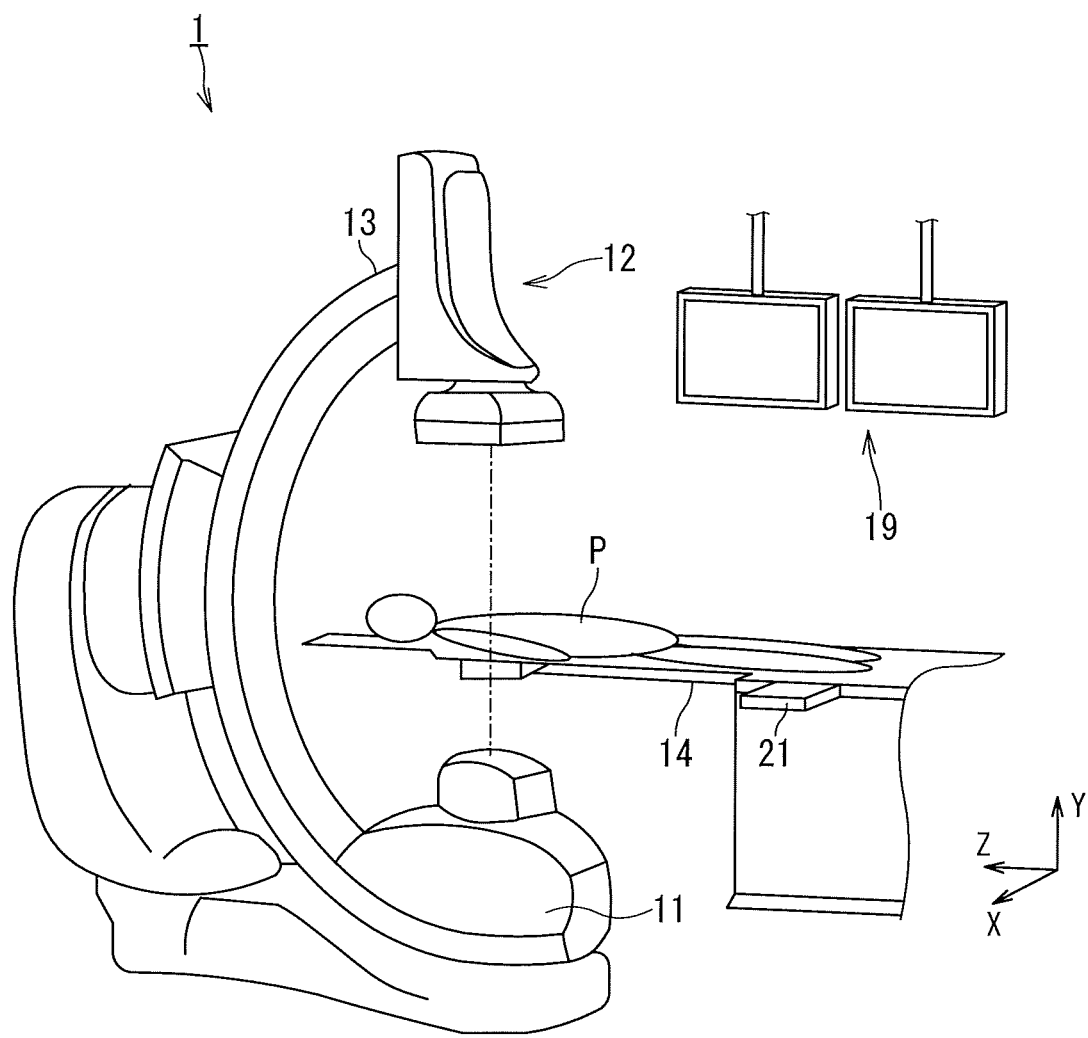
FIG. 2 is a perspective view showing an appearance of a part of the X-ray imaging apparatus according to the embodiment.
Figure 9:
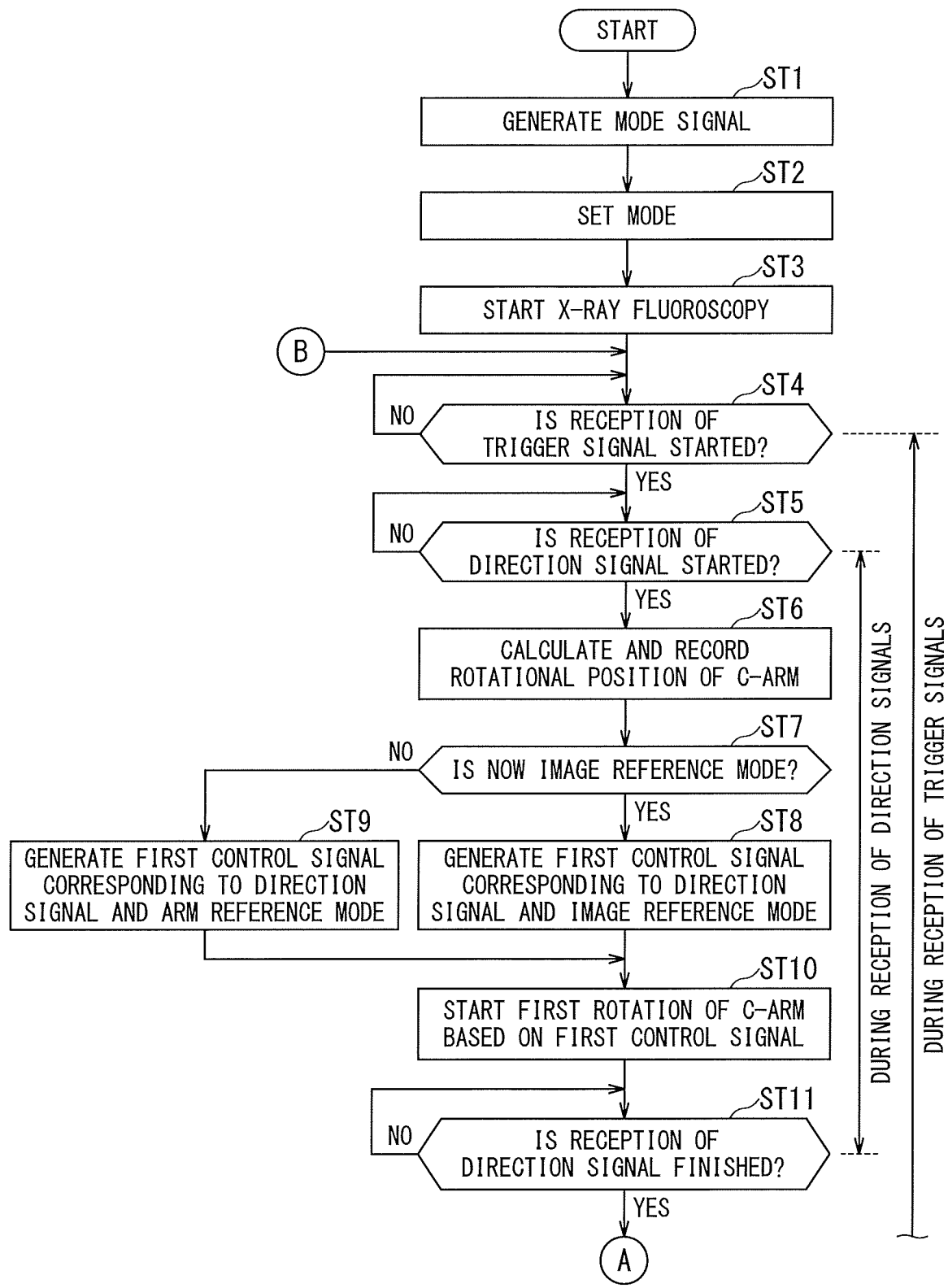
Figure 10:
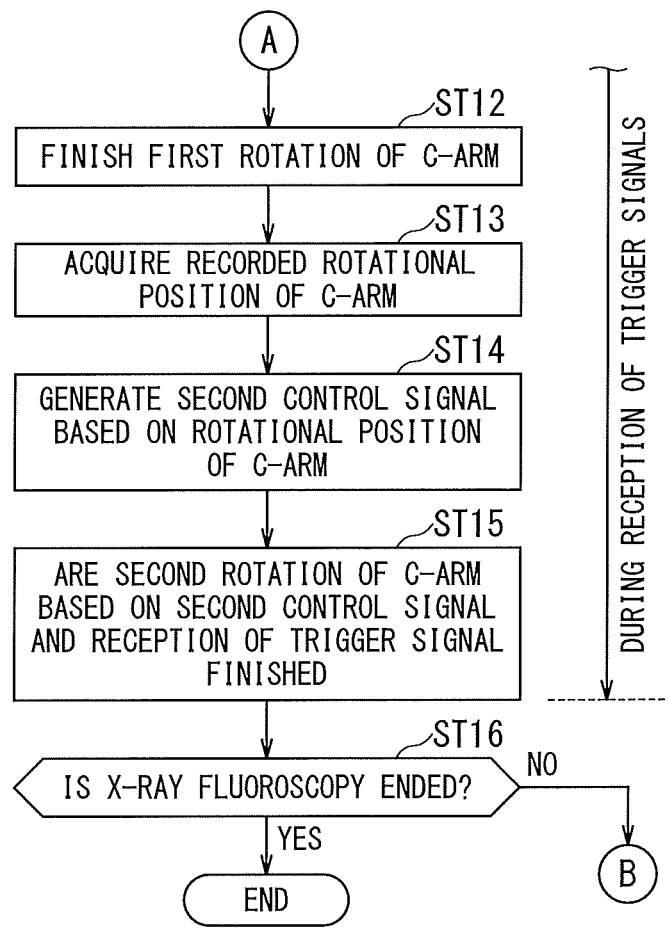
Figure 11A:
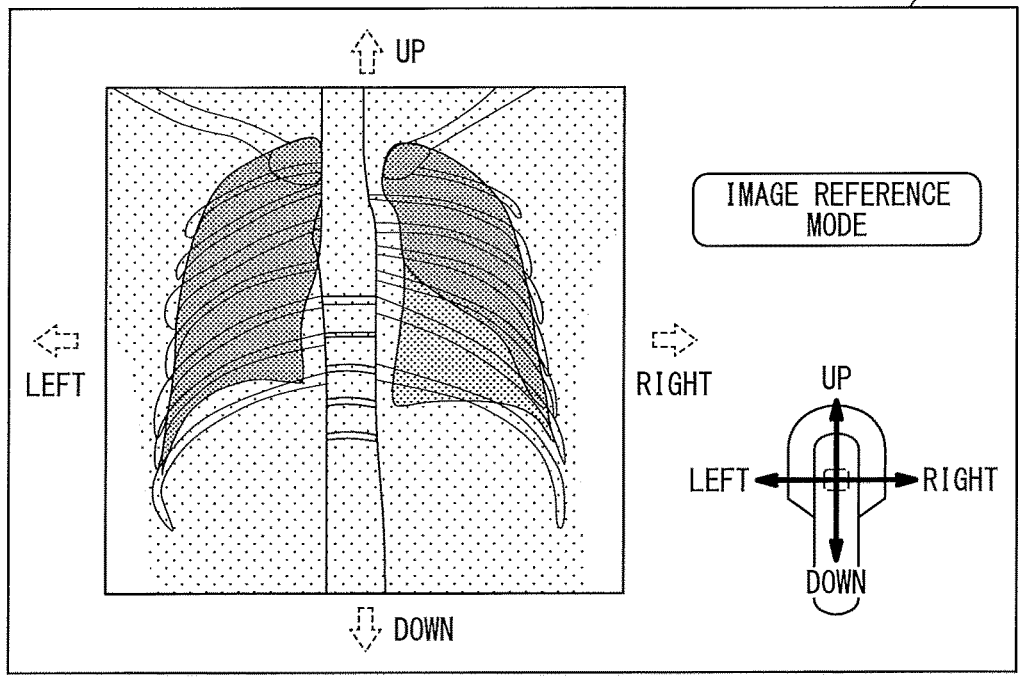
Figure 11B:
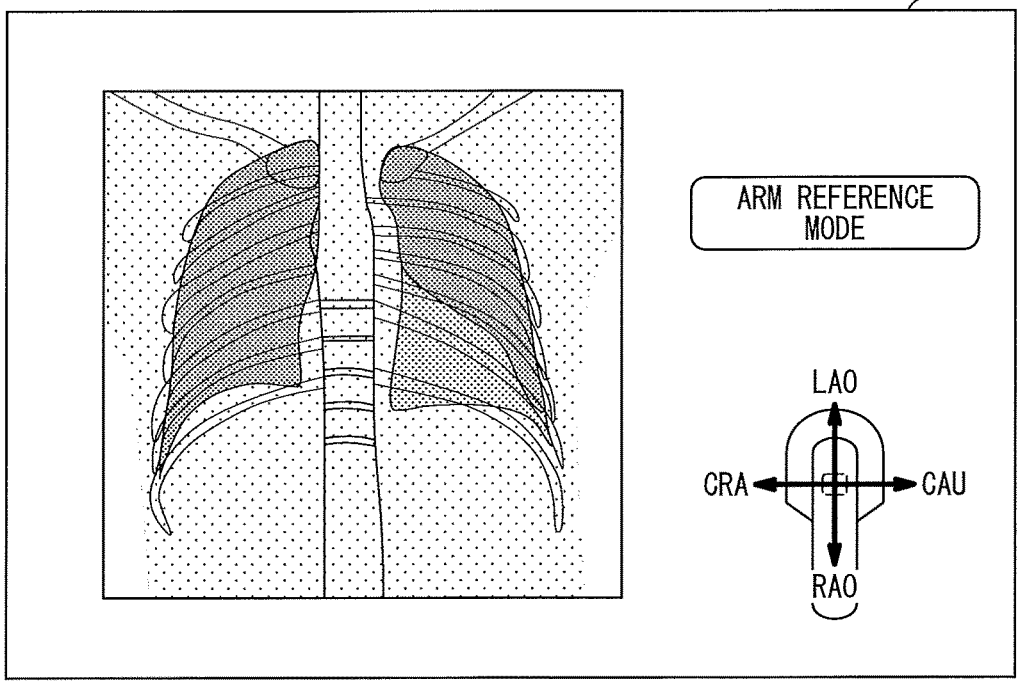
Figures 12A, 12B:
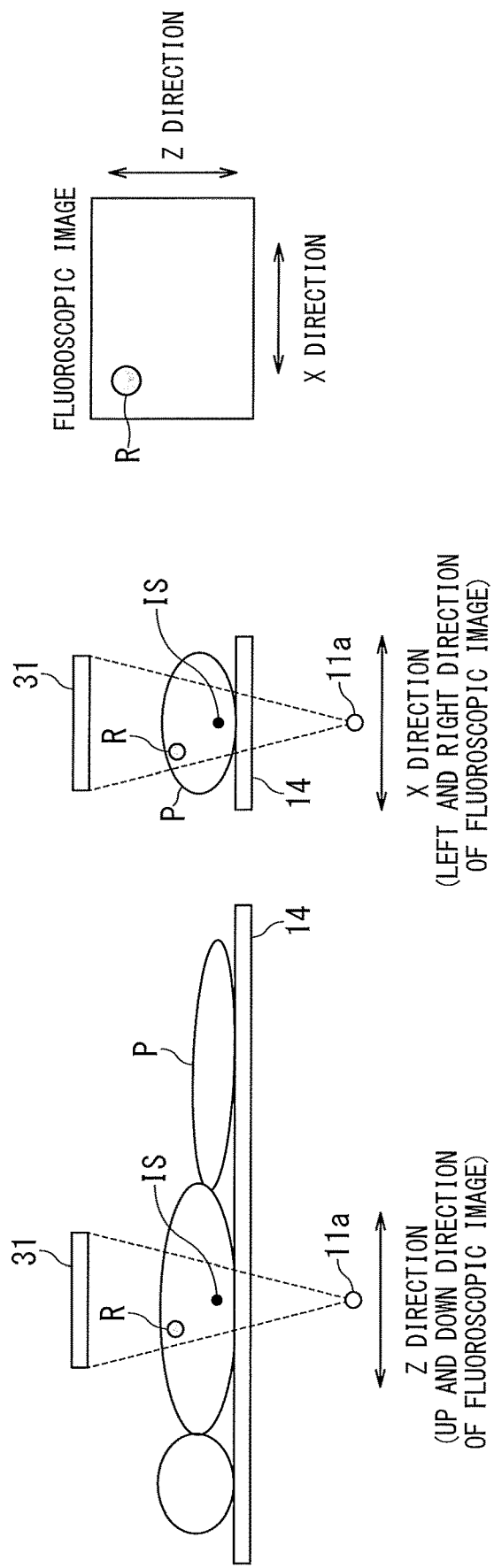
Figures 13A, 13B:
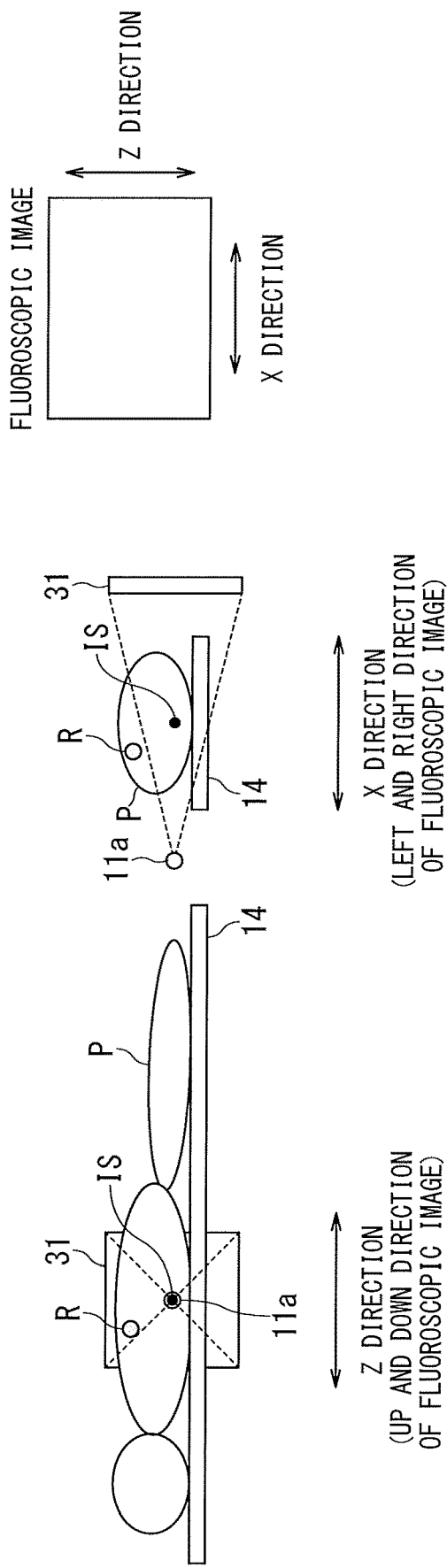
Figures 14A, 14B:
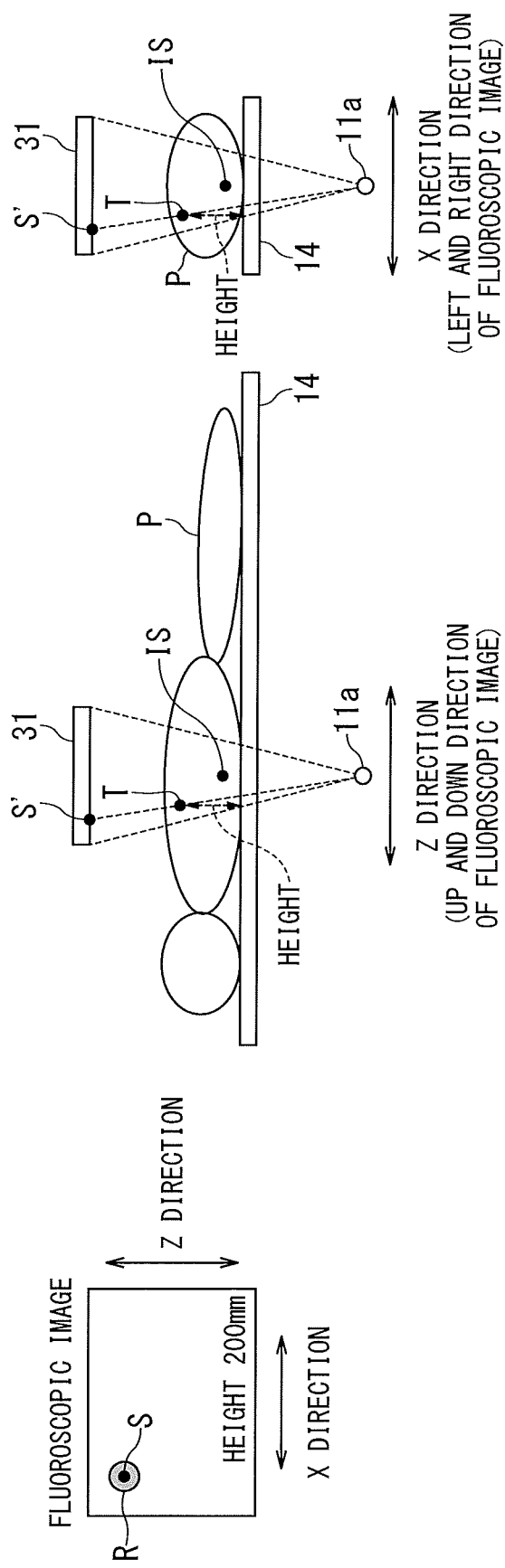
Figures 15A, 15B:
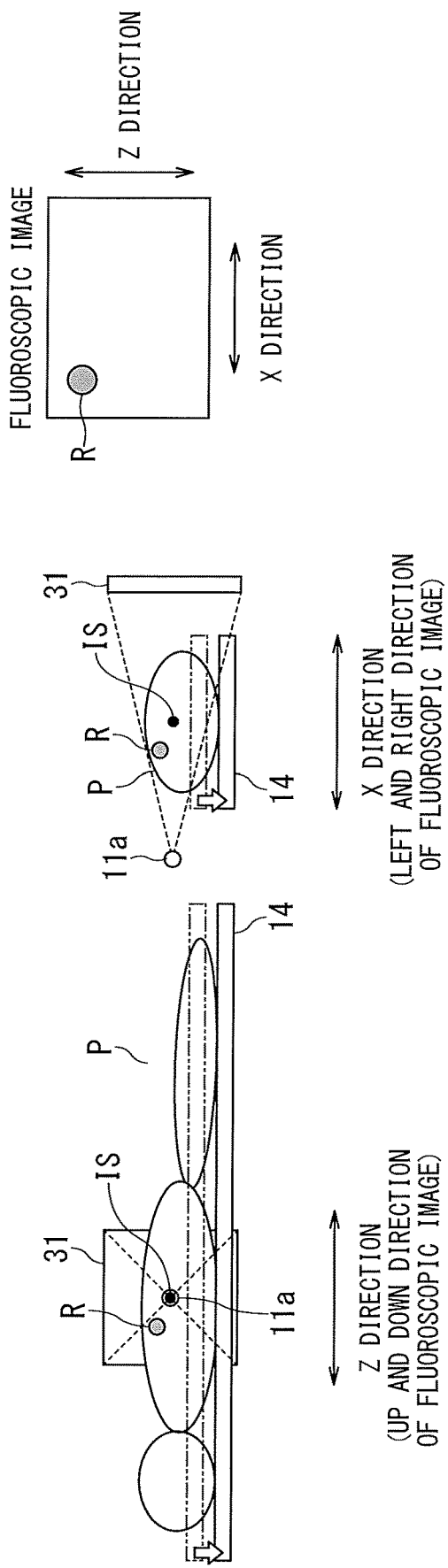

Each of FIGS. 7A and 7B is a diagram for explaining a method of generating a first control signal according to a mode and a direction signal in the X-ray imaging apparatus according to the embodiment;

FIG. 8A is a diagram showing a relationship between the mode and direction signal and the first control signal in the case where the input interface is provided on the right side of the patient as shown in FIG. 2, in the X-ray imaging apparatus according to the embodiment;

FIG. 8B is a diagram showing a relationship between the mode and direction signal and the first control signal in the case where the input interface is provided on the left side of the patient, in the X-ray imaging apparatus according to the embodiment;

FIG. 9 is a diagram showing, as a flowchart, operations of the X-ray imaging apparatus according to the embodiment;

FIG. 10 is a diagram showing, as a flowchart, operations of the X-ray imaging apparatus according to the embodiment;

FIG. 11A is a diagram showing a display example of image reference mode data, in the X-ray imaging apparatus according to the embodiment;

FIG. 11B is a diagram showing a display example of arm reference mode data, in the X-ray imaging apparatus according to the embodiment;

FIG. 12A is a diagram showing a state of the C-arm provided in the X-ray imaging apparatus according to the embodiment before the first rotation;

FIG. 12B is a diagram showing the fluoroscopic image displayed in the state shown in FIG. 12A, in the X-ray imaging apparatus according to the embodiment;

FIG. 13A is a diagram showing a state of the C-arm provided in the X-ray imaging apparatus according to the embodiment after the first rotation;

FIG. 13B is a diagram showing the fluoroscopic image displayed in the state shown in FIG. 13A, in the X-ray imaging apparatus according to the embodiment;

FIG. 14A is a diagram showing the fluoroscopic image displayed in a state of the C-arm provided in the X-ray imaging apparatus according to the embodiment before the first rotation;

FIG. 14B is a diagram showing a two-dimensional position of the target part set by the fluoroscopic image or the like shown in FIG. 14A, in the X-ray imaging apparatus according to the embodiment;

FIG. 15A is a diagram showing a state, under the position control of the table, of the C-arm provided in the X-ray imaging apparatus according to the embodiment after the first rotation; and FIG. 15B is a diagram showing the fluoroscopic image displayed in the state shown in FIG. 15A, in the X-ray imaging apparatus according to the embodiment.

DETAILED DESCRIPTION

An X-ray imaging apparatus according to embodiments will be described in detail with reference to the drawings.

The X-ray imaging apparatus according to an embodiment includes an X-ray generator, an X-ray detector, an input interface, and processing circuitry. The X-ray generator is configured to generate X-rays. The X-ray detector is configured to detect the X-rays. The arm is configured to hold the X-ray generator and the X-ray detector. The input interface is configured to generate a direction signal for determining a rotating direction of the arm. The processing circuitry is configured to: display, on a display, an image based on the X-rays detected by the X-ray detector; control, based on a first control signal according to the direction signal, a rotating mechanism of the arm so that the arm performs a first rotation; and control, in response to an end of the first rotation, based on a second control signal, the rotating mechanism so that the arm performs a second rotation which returns the arm toward a position before the first rotation, the position being stored in a memory circuit.

Figure 1:
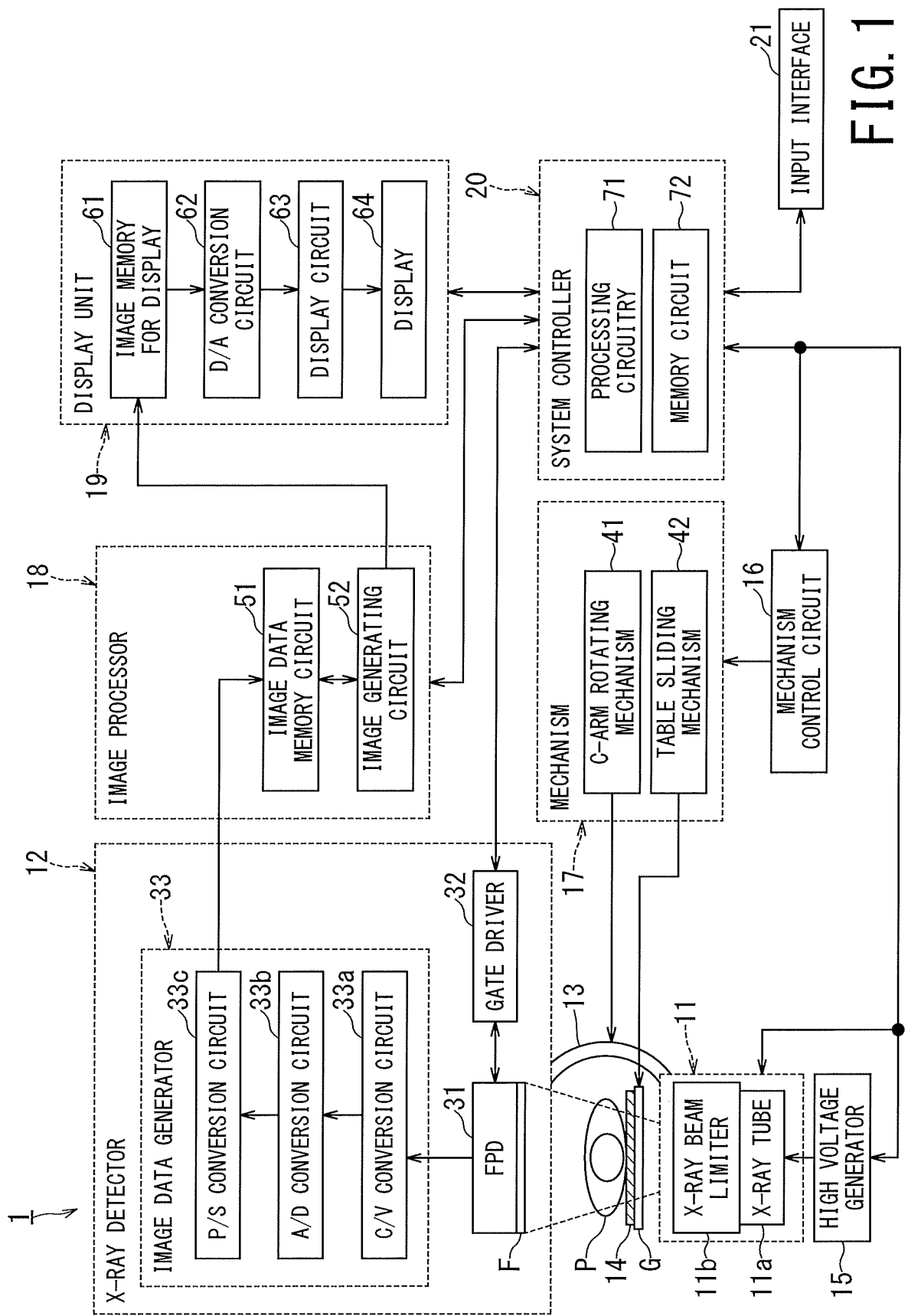
FIG. 1 is a schematic diagram showing a configuration of an X-ray imaging apparatus according to an embodiment.

FIG. 1 is a schematic diagram showing a configuration of an X-ray imaging apparatus according to an embodiment. FIG. 2 is a perspective view showing an appearance of a part of the X-ray imaging apparatus according to the embodiment.

FIGS. 1 and 2 show an X-ray imaging apparatus 1 according to an embodiment. The X-ray imaging apparatus 1 is able to support the IVR surgery using X-ray fluoroscopy. The IVR surgery using the X-ray fluoroscopy means treatment using a catheter during the X-ray fluoroscopy. In the IVR surgery using the X-ray fluoroscopy, the X-ray imaging apparatus 1 generates fluoroscopic images in chronological order and displays them in real time.

The X-ray imaging apparatus 1 includes an X-ray generator 11, an X-ray detector 12, a C-arm 13, a table 14, a high voltage generator 15, a mechanism control circuit 16, a mechanism 17, an image processor 18, a display unit 19, a system controller 20, and an input interface 21.

The X-ray generator 11 includes an X-ray tube 11a and an X-ray beam limiter 11b. The X-ray tube 11a irradiates, under the control of the system controller 20, a patient P with X-rays. The X-ray tube 11a is a vacuum tube for generating the X-rays. The X-ray tube 11a accelerates thermionic electrons emitted from a cathode (filament) by a high voltage applied between an anode and the cathode. Then, X-ray tube 11a generates the X-rays by causing the accelerated thermionic electrons to collide with the tungsten anode.

The X-ray beam limiter 11b controls, under the control of the system controller 20, sliding of diaphragms thereof, and forms an X-ray pyramid (cone beam) with respect to the X-rays emitted from the X-ray tube 11a. The X-ray beam limiter 11b is arranged between the X-ray tube 11a and the patient P. The X-ray beam limiter 11b narrows down the X-ray beam emitted from the X-ray tube 11a to a predetermined visual field size in order not to expose a part other than a target part of the patient P.

The X-ray detector 12 two-dimensionally detects, under the control of the system controller 20, the X-rays transmissive through the patient P. The X-ray detector 12 includes a flat panel detector (FPD) 31, a gate driver 32, and an image data generator 33.

The X-ray detector 12 includes a direct conversion system which directly converts the X-rays into electric charges, and an indirect conversion system which converts the X-rays into electric charges and then converts them into electric charges. In the embodiment, the former is described as an example, but the latter may be used.

The FPD 31 is an example of an X-ray detector configured by arranging minute elements two-dimensionally in the column and line directions. Each element of the FPD 31 includes an X-ray detecting element, a photoelectric film, a charge storage capacitor, and a thin film transistor (TFT). The X-ray detecting element senses the X-rays. The photoelectric film generates charges according to the incident X-ray dose. The charge storage capacitor accumulates the charges generated in the photoelectric film. The TFT reads the charges accumulated in the charge storage capacitor as raw data of an X-ray transmission image (fluoroscopic image or radiographic image) at a predetermined timing. It should be noted that the raw data of the X-ray fluoroscopic image may be converted using the non dosimeter dosimetry (NDD) method, and the surface dose data of the X-ray transmission image may be generated.

The gate driver 32 is installed to extract charges from the FPD 31. The image data generator 33 generates image data of an X-ray transmission image based on the raw data (or surface dose data) of the X-ray transmission image output from the X-ray detector 12.

The image data generator 33 includes a charge/voltage conversion circuit 33a, an analog to digital (A/D) conversion circuit 33b, and a parallel/serial conversion circuit 33c.

The charge/voltage conversion circuit 33a converts the electric charge read from the FPD 31 into a voltage. The A/D conversion circuit 33b converts the output of the charge/voltage conversion circuit 33a into digital signals. The parallel/serial conversion circuit 33c converts the digitally converted image data read in parallel on a line basis from the FPD 31 into serial signals.

In the X-ray imaging apparatus 1, in order to perform X-ray automatic exposure control, a photo pickup (for example, a fluorescent lighting type fiber detector) F may be incorporated in front of the FPD 31. In the case of X-ray examination for the X-ray fluoroscopy, X-rays for the X-ray fluoroscopy are detected by the FPD 31, and the feedback loop may be configured so that the luminance of the display 64 of the display unit 19 becomes constant, based on the detection signal. Alternatively, the feedback loop may be configured so that the average value of pixel signals (or video signals) imaged by the FPD 31 becomes constant.

In addition, in FIG. 1, the imaging system of the C-arm structure included in the X-ray imaging apparatus 1 shows a case where the X-ray generator 11 is an under table positioned below the table 14. However, it is not limited to that case. For example, the X-ray generator 11 may be an over table positioned above the table 14.

The C-arm 13 integrally holds the X-ray generator 11 and the X-ray detector 12. It should be noted that the arm holding the X-ray generator 11 and the X-ray detector 12 as one body is not limited to the so-called C-arm based on the "C" shape. For example, the arm integrally holding the X-ray generator 11 and the X-ray detector 12 may be a so-called Ω arm based on "Ω" shape.

The table 14 is able to place the patient P thereon.

The high voltage generator 15 supplies, under the control of the system controller 20, high voltage power to the X-ray tube 11a.

The mechanism control circuit 16 is a motor circuit for supplying, under the control of the system controller 20, electricity to the mechanism 17 to rotate the C-arm 13 or to slide the table 14.

The mechanism 17 includes a C-arm rotating mechanism 41 and a table sliding mechanism 42. The C-arm rotating mechanism 41 moves each motor unit constituting the C-arm rotating mechanism 41 under the control of the system controller 20 via the mechanism control circuit 16. Thus, the C-arm rotating mechanism 41 rotates the C-arm 13 holding the X-ray generator 11 and the X-ray detector 12 in a circular arc direction of the C-arm 13, or rotates the C-arm 13 holding the X-ray generator 11 and the X-ray detector 12 about a fulcrum of the C-arm 13.

The rotation of the C-arm 13 in the circular arc direction corresponds to a rotation in a direction of the cranial view (CRA) or a rotation in a direction of the caudal view (CAU). The rotation of the fulcrum center of the C-arm 13 corresponds to a rotation in a direction of the left anterior oblique view (LAO) or a rotation in a direction of the right anterior oblique view (RAO). It should be noted that the rotation of the C-arm 13 in the circular arc direction may have a configuration corresponding to the rotation in the direction of the LAO and the rotation in the direction of the RAO, and corresponding to the rotation of the direction of the CRA and the rotation of the direction of the CAU.

The table sliding mechanism 42 moves, under the control of the system controller 20 via the mechanism control circuit 16, each power unit constituting a table holder G which holds the table 14. Thus, the table sliding mechanism 42 is able to slide the table holder G in the left-right direction (the X-axis direction shown in FIG. 2 or the opposite direction), in the vertical direction (the Y-axis direction shown in FIG. 2 or the opposite direction), or in the body axis direction (the Z-axis direction shown in FIG. 2 or the opposite direction).

The image processor 18 includes an image data memory circuit 51 and an image generating circuit 52. The image data memory circuit 51 stores, under the control of the system controller 20, the image data sequentially output from the image data generator 33 line by line or frame unit.

Under the control of the system controller 20, the image generating circuit 52 performs image processing on the image data stored in the image data memory circuit 51, and records the image data after the image processing in the image data memory circuit 51. Examples of the image processing include enlargement/gradation/spatial filter processing of image data of X-ray transmission image, minimum value/maximum value tracing processing of image data accumulated in time series, subtraction processing, addition processing for removing noise, or the like.

The display unit 19 synthesizes, under the control of the system controller 20, data from text/graphic information such as X-ray emitting conditions and the like provided from the system controller 20 and from the image data of the X-ray transmission image processed by the image processor 18, and displays it. Specifically, the display unit 19 includes an image memory 61 for display, a digital to analog (D/A) converter 62, a display circuit 63, and a display 64.

The image memory 61 for display synthesizes data from the image data of the X-ray transmission image, and from the X-ray emitting conditions (tube voltage, tube current, fluoroscopic time, dose information, etc.) converted by the system controller 20, or from numerals and various characters which are incidental data of the image data, and temporarily records the synthesized data.

The D/A converter 62 converts the image data of the X-ray transmission image and the incidental data into analog signals.

The display circuit 63 is a circuit for format conversion for converting the analog signals into a TV format, thereby generating video signals.

The display 64 is a display device displaying the video signals, such as a liquid crystal display panel, a plasma display panel, an organic electro luminescence (EL) panel or the like.

The system controller 20 includes processing circuitry 71 and a memory circuit 72. The system controller 20 controls the entire X-ray imaging apparatus 1 according to an instruction of an operator input from the input interface 21. The system controller 20 performs control so as to perform an X-ray radiography for the purpose of generating an image used for diagnosis or the X-ray fluoroscopy with a reduced dose compared to the X-ray radiography. The X-ray fluoroscopy is roughly divided into a continuous fluoroscopy and a pulse fluoroscopy. The pulse fluoroscopy means a fluoroscopic method of intermittently emitting X-rays with intermittent rectangular waves unlike the continuous fluoroscopy. According to the pulse fluoroscopy, the continuity (frame rate) of fluoroscopic images is somewhat inferior to the continuous fluoroscopy, but the exposure dose to the patient can be suppressed compared to the continuous fluoroscopy.

The processing circuitry 71 means any one of dedicated or general central processing unit (CPU) and a micro processor unit (MPU), an application specific integrated circuit (ASIC), and a programmable logic device. The programmable logic device may be, for example, any one of a simple programmable logic device (SPLD), a complex programmable logic device (CPLD), a field programmable gate array (FPGA) and the like. The processing circuitry 71 achieves functions to be described later by reading out and executing a program stored in the memory circuit 72 or directly incorporated in the processing circuitry 71.

The processing circuitry 71 may be a single processing circuit or a combination of multiple processing circuit elements. In the latter case, the memory circuit 72 includes multiple memory elements each storing an element of a program that the processing circuitry 71 executes, and each corresponding to the processing circuit. Alternatively, in the latter case, the memory circuit 72 includes a single memory storing the program that the processing circuitry 71 executes, and corresponding to the multiple processing circuits.

The memory circuit 72 includes a semiconductor memory element such as a random access memory (RAM), a flash memory and the like, a hard disk, an optical disk and the like. The memory circuit 72 may be a portable media such as a universal serial bus (USB) memory, a digital video disk (DVD) and the like. The memory circuit 72 stores various processing programs (in addition to application programs, an operating system (OS) and the like are also included), data required for execution of the programs.

The input interface 21 includes an input device which is able to be operated by an operator, and an input circuit for inputting a signal from the input device. The input device has a structure capable of an interactive (two-way) communication interface including a display panel, a keyboard, various switches, a keypad switch, a mouse, and the like. The input circuit generates, when the operator operates the input device, a signal corresponding to the operation and outputs the signal to the system controller 20. In FIG. 2, the case where the input interface 21 is provided on the right side of the patient P is shown, but the present invention is not limited to this case. For example, the input interface 21 may be provided on the left side of the patient P.

The input interface 21 transmits, to the system controller 20, patient information of the patient P and a signal corresponding to the optimum X-ray emitting condition and the like for the target part of the patient P by the operation of the operator. The patient information includes an examination site, examination method, physique (body thickness), past diagnosis history, and the like.

The input interface 21 generates a direction signal for determining the rotating direction of the C-arm 13, which will be described later, by an operation of the operator, and transmits it to the system controller 20. In addition, the input interface 21 may also generate a mode signal and a trigger signal, which will be described later, by operations of the operator, and transmit the mode signal and the trigger signal to the system controller 20.

Figure 3:
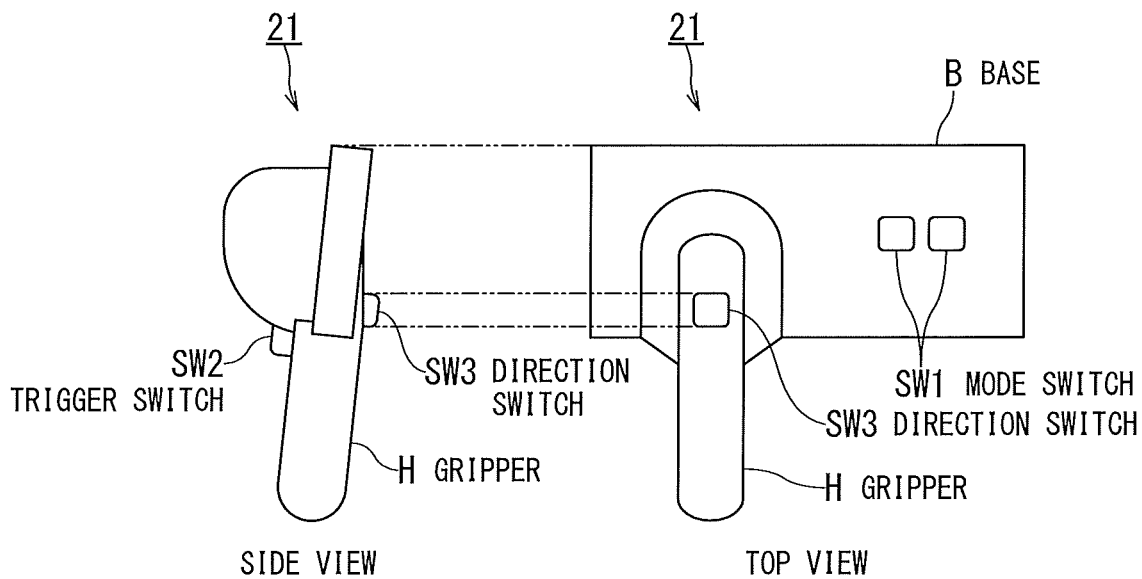
FIG. 3 is a diagram showing a configuration example of an input interface provided in the X-ray imaging apparatus according to the embodiment.
Figure 4:
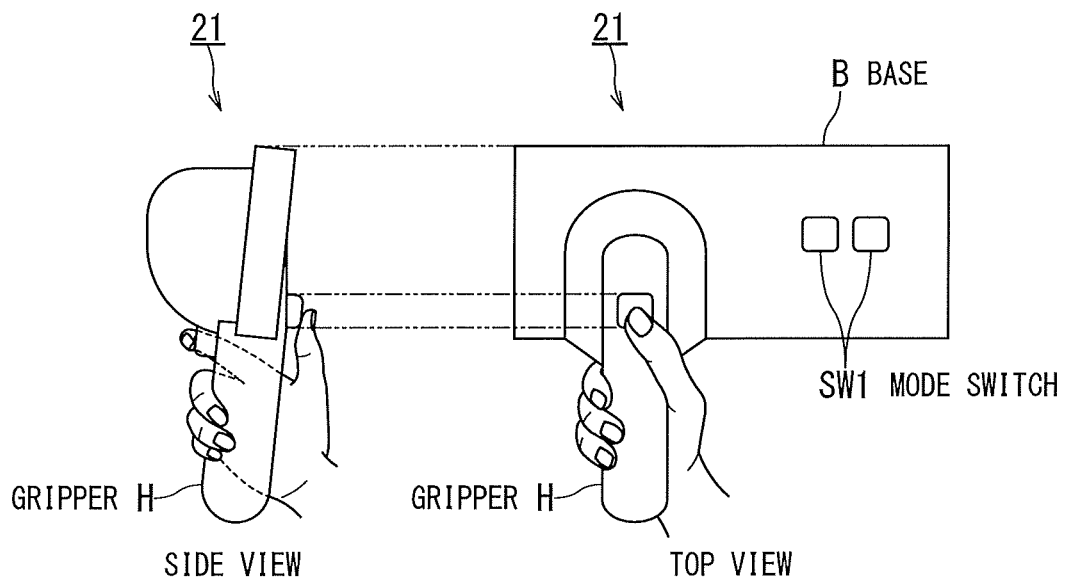
FIG. 4 is a diagram showing an example of holding of the input interface provided in the X-ray imaging apparatus according to the embodiment.
Figure 5:
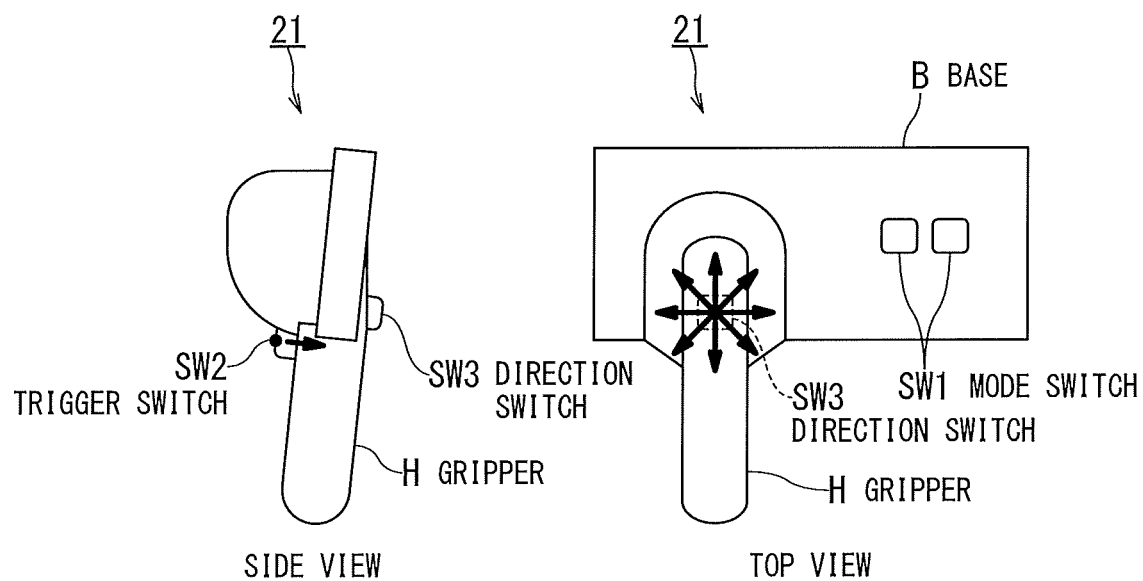
FIG. 5 is a diagram showing an operation example of the input interface provided in the X-ray imaging apparatus according to the embodiment.

FIG. 3 is a diagram showing a configuration example of the input interface 21 provided in the X-ray imaging apparatus 1. FIG. 4 is a diagram showing an example of holding of the input interface 21 provided in the X-ray imaging apparatus 1. FIG. 5 is a diagram showing an operation example of the input interface 21 provided in the X-ray imaging apparatus 1.

As shown in FIG. 3, the input interface 21 includes a mode setting unit (for example, a mode switch SW1), a trigger switch SW2, a direction switch SW3, a gripper H, and a base B. The mode switch SW1 is provided on a top side of the base B. In FIG. 3, the mode switch SW1 is shown as switching the mode by two switch elements, but it is not limited to this case. It may be switched by one switch element. The mode setting unit may be constituted by a hardware switch such as a slide type switch, an electrostatic sensor type switch, etc. besides a push button type mode switch SW1. The mode setting unit may be constituted by a software switch for performing a click operation, a drag and drop operation, a long push operation, etc. on an icon on a display screen. The gripper H is fixed to the top side of the base B. The trigger switch SW2 is disposed on a back side of the gripper H, and the direction switch SW3 is disposed on the top side of the gripper H.

As shown in FIG. 4, when an operator who operates the catheter or an operator who is an assistant rotating the C-arm grips the gripper H, a finger of the operator, for example, an index finger is able to touch the trigger switch SW2 of the back side. Further, when the operator grips the gripper H, a finger of the operator, for example the thumb is able to touch the direction switch SW3 of the top side.

As shown in FIG. 5, the input interface 21 has such a structure that the operator is able to press the mode switch SW1. As a result, the operator is able to select an arbitrary mode from "arm reference mode" and "image reference mode". The input interface 21 generates, when the mode switch SW1 is pressed down, a mode signal indicating one of "arm reference mode" and "image reference mode", and transmits the mode signal to the system controller 20 (shown in FIG. 1). "Arm reference mode" and "image reference mode" will be described later.

The input interface 21 has a structure capable of pressing the trigger switch SW2 in an arrow shown in the side view of FIG. 5 by the index finger of the operator holding the gripper H. Further, the input interface 21 has a structure capable of returning, when the index finger of the operator holding the gripper H releases the pressing operation of the trigger switch SW2, the trigger switch SW2 to the position before the pressing operation. The input interface 21 generates, when the trigger switch SW2 is pressed down, a trigger signal and transmits it to the system controller 20 (shown in FIG. 1).

The input interface 21 has a structure capable of tilting the direction switch SW3 in either one of the upward and downward arrows shown in the top view of FIG. 5, of the lateral arrows shown in the top view of FIG. 5, or of the oblique arrows shown in the top view of FIG. 5, by the thumb of the operator holding the gripper H. The input interface 21 has a structure capable of returning, when the thumb of the operator holding the gripper H releases the tilting operation of the direction switch SW3, the direction switch SW3 to the position before the operation. When the direction switch SW3 is operated to be tilted in an arbitrary direction while the trigger switch SW2 is pressed down, the input interface 21 generates a direction signal for determining the rotating direction of the C-arm 13, and transmits the signal to the system controller 20 (shown in FIG. 1). In FIG. 5, the eight directions obtained by dividing 360° into eight are indicated by arrows, but the present invention is not limited to this case, and any number of 360° may be divided.

It should be noted that the configuration and operation of the input interface 21 is not limited to the case of the input interface 21 shown in FIGS. 3 and 5. For example, the direction switch SW3 may be constituted by a joystick capable of being tilted.

Subsequently, functions of the X-ray imaging apparatus 1 will be described.

Figure 6:
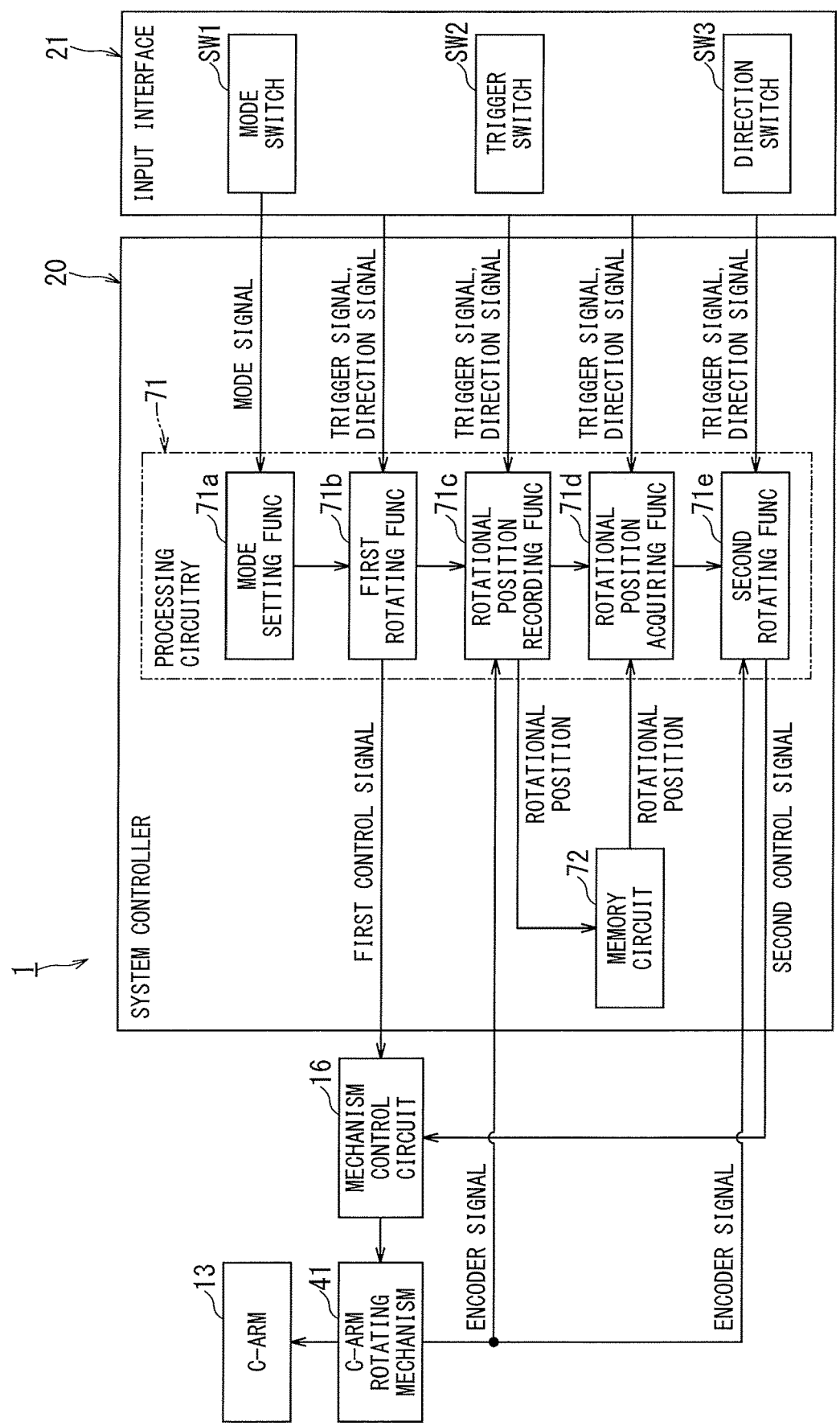
FIG. 6 is a block diagram showing functions of the X-ray imaging apparatus according to the embodiment.

FIG. 6 is a block diagram showing functions of the X-ray imaging apparatus 1.

By the execution of a program by the processing circuitry 71, the X-ray imaging apparatus 1 achieves a mode setting unit (for example, a mode setting function) 71a, a first rotating unit (for example, a first rotating function) 71b, a rotational position recording unit (rotational position recording function) 71c, rotational position acquiring unit (for example, rotational position acquiring function) 71d, and a second rotating unit (for example, second rotating function) 71e. It should be noted that the whole or a part of the functions 71a to 71e is not limited to being realized by the execution of the program but may be achieved by a circuit such as an ASIC provided in the X-ray imaging apparatus 1.

The mode setting function 71a includes a function of receiving a mode signal indicating one of "arm reference mode" and "image reference mode" from the mode switch SW1 of the input interface 21, and a function of setting a mode corresponding to the mode signal. In the embodiment, the arm reference mode means a mode for setting the rotating direction of the C-arm 13, as a direction indicated by the tilting operation of the direction switch SW3 shown in FIG. 5C. The image reference mode means a mode for setting the rotating direction of the C-arm 13 determined by setting a direction indicated by the tilting operation of the direction switch SW3, as a moving direction of an imaging region of the fluoroscopic image displayed.

The first rotating function 71b includes a function of receiving a trigger signal from the trigger switch SW2 of the input interface 21, and a function of receiving a direction signal from the direction switch SW3 of the input interface 21. The first rotating function 71b includes a function of generating, when receiving the direction signal during reception of the trigger signals, the first control signal according to the direction signal, based on the mode and direction signal set by the mode setting function 71a, and a function of transmitting the first control signal to the mechanism control circuit 16.

The trigger signal is generated by the trigger switch SW2 when the trigger switch SW2 is pressed by the operator. The direction signal is generated by the direction switch SW3 when the direction switch SW3 is tilted by the operator. The mechanism control circuit 16 controls the C-arm rotating mechanism 41, based on the control signal from the first rotating function 71b to perform a first rotation of the C-arm 13 in the direction of CRA, CAU, LAO, RAO, or a combination thereof.

Each of FIGS. 7A and 7B is a diagram for explaining a method of generating the first control signal according to the mode and the direction signal in the X-ray imaging apparatus 1.

In FIGS. 7A and 7B, a case where a direction indicated by the tilting operation of the direction switch SW3 by the operator is "left" will be considered. When the input interface 21 is provided on the right side of the patient P as shown in FIG. 2, and when the arm reference mode shown in FIG. 7A is set, a first control signal is generated such that the C-arm 13 performs the first rotation in the CRA direction, that is, the direction in which the FPD 31 moves to the head side of the patient P. Similarly, when the image reference mode shown in FIG. 7B is set, a first control signal is generated such that the C-arm 13 performs the first rotation in the RAO direction, that is, the direction in which the imaging region of the fluoroscopic image moves to the left side.

Further, in FIGS. 7A and 7B, a case where the direction of the tilting operation by the operator is "up" will be considered. When the input interface 21 is provided on the right side of the patient P as shown in FIG. 2, and when the arm reference mode shown in FIG. 7A is set, a first control signal is generated such that the C-arm 13 performs the first rotation in the LAO direction, that is, the direction in which the FPD 31 moves to the left side of the patient P. Similarly, when the image reference mode shown in FIG. 7B is set, a first control signal is generated such that the C-arm 13 performs the first rotation in the CRA direction, that is, the direction in which the imaging region of the fluoroscopic image moves to the upper side.

FIG. 8A is a diagram showing a relationship between the mode and direction signal and the first control signal in the case where the input interface 21 is provided on the right side of the patient P as shown in FIG. 2, in the X-ray imaging apparatus 1.

According to FIG. 8A, as described with reference to FIG. 7A, in the case of the arm reference mode and the direction signal "left", a first control signal is generated such that the C-arm 13 performs the first rotation in the CRA direction. According to FIG. 8A, as described with reference to FIG. 7B, in the case of the image reference mode and the direction signal "left", a first control signal is generated such that the C-arm 13 performs the first rotation in the RAO direction. Further, according to FIG. 8A, as described with reference to FIG. 7A, in the case of the arm reference mode and the direction signal "up", a first control signal is generated such that the C-arm 13 performs the first rotation in the LAO direction. According to FIG. 8A, as described with reference to FIG. 7B, in the case of the image reference mode and the direction signal "up", a first control signal is generated such that the C-arm 13 performs the first rotation in the CRA direction.

Further, a case where the direction of the tilting operation by the operator is "upper left" will be considered. When the arm reference mode is set, a first control signal is generated such that the C-arm 13 performs the first rotation in a direction of the CRA in which the FPD 31 moves to the head side of the patient P, and of the LAO in which the FPD 31 moves to the left side of the patient P. When the image reference mode is set, a first control signal is generated such that the C-arm 13 performs the first rotation in a direction of the RAO and CRA in which the imaging region of the fluoroscopic image moves to the head and left sides of the patient P. When a direction of the tilting operation by the operator is "upper left 45-degree", and when the rotation speed in the single RAO direction is set as "100%", each rotation speed in the RAO and CRA directions may be "50%".

It should be noted that the relationship between the other combination of the mode and direction signal and the control signal is shown in FIG. 8A, and the explanation is omitted.

A relationship between the mode and direction signal and the first control signal in a case where the input interface 21 is provided on the left side of the patient P (not shown) is shown in FIG. 8B. In FIG. 8B, part of FIG. 8A is modified. FIG. 8B is a diagram showing a relationship between the mode and direction signal and the first control signal in the case where the input interface 21 is provided on the left side of the patient P, in the X-ray imaging apparatus 1.

Returning to the explanation of FIG. 6, the rotational position recording function 71c includes a function of receiving the trigger signal from the trigger switch SW2 of the input interface 21, and a function of receiving the direction signal from the direction switch SW3 of the input interface 21. The rotational position recording function 71c includes a function of receiving an encoder signal from the C-arm rotating mechanism 41 when starting of the reception of the direction signal during receiving the trigger signals, and a function of calculating, based on the encoder signal, the rotational position (fluoroscopic angle) of the C-arm 13 and recording it in the memory circuit 72.

In the embodiment, the rotational position recording function 71c acquires the encoder signal from a rotary encoder (not shown) attached to rollers (not shown) constituting the C-arm rotating mechanism 41. Then, the rotational position recording function 71c calculates, based on the acquired encoder signal, the rotational position of the C-arm 13. The rotary encoder detects encoder information which is the basis of the rotational position of the C-arm 13 by converting the mechanical displacement amount of the rotation of the roller for operating the C-arm 13 into an electric signal and processing the electric signal.

The rotational position acquiring function 71d includes a function of receiving the trigger signal from the trigger switch SW2 of the input interface 21, and a function of receiving the direction signal from the direction switch SW3 of the input interface 21. The rotational position acquiring function 71d includes a function of acquiring the rotational position, stored in the memory circuit 72, of the C-arm 13 from the memory circuit 72 when reception of the direction signal is finished during reception of the trigger signals.

The second rotating function 71e includes a function of receiving the trigger signal from the trigger switch SW2 of the input interface 21, and a function of receiving the direction signal from the direction switch SW3 of the input interface 21. The second rotating function 71e includes a function of receiving the encoder signal from the C-arm rotating mechanism 41 when the reception of the direction signal is finished during reception of the trigger signal, and a function of calculating, based on the encoder signal, the rotational position of the C-arm 13. The second rotating function 71e includes a function of generating, based on the calculated rotational position of the C-arm 13, a second control signal for returning to the rotational position of the C-arm 13 acquired by the rotational position acquiring function 71d, and a function of transmitting the second control signal to the mechanism control circuit 16.

The mechanism control circuit 16 controls, based on the second control signal from the second rotating function 71e, the C-arm rotating mechanism 41 to perform the second rotation of the C-arm 13 in the direction of CRA, CAU, LAO, RAO, or a combination thereof. That is, when the reception of the direction signal is finished during reception of the trigger signals, the second rotating function 71e returns the C-arm 13 to the rotational position before reception of the direction signal.

Next, operations of the X-ray imaging apparatus 1 will be described with reference to FIGS. 6, 9, and 10.

Each of FIGS. 9 and 10 is a diagram showing, as a flowchart, the operations of the X-ray imaging apparatus 1.

The input interface 21 generates a mode signal indicating one of "arm reference mode" and "image reference mode" by operating the mode switch SW1 of the input interface 21 (step ST1). The mode setting function 71a receives the mode signal generated in step ST1 from the input interface 21, and sets a mode corresponding to the mode signal (step ST2).

The X-ray imaging apparatus 1 starts, when the fluoroscopy start switch (not shown) of the input interface 21 is pressed by the operator, X-ray fluoroscopy for the patient P according to the set X-ray emitting condition (step ST3). During the X-ray fluoroscopy, the patient P is subjected to IVR surgery using the X-ray fluoroscopy. The IVR surgery using the X-ray fluoroscopy means mainly treatment using a catheter during the X-ray fluoroscopy. The X-ray imaging apparatus 1 generates fluoroscopic images in chronological order and displays, on the display 64 (shown in FIG. 1), them in real time in IVR surgery using the X-ray fluoroscopy. During the X-ray fluoroscopy, the X-ray imaging apparatus 1 fixes, unless otherwise indicated, the rotational position of the C-arm 13 to a working angle and performs the X-ray fluoroscopy at the fixed angle to display 64 (or display unit 19) the fluoroscopic images.

The first rotating function 71b determines whether or not the trigger switch SW2 of the input interface 21 is pressed by the operator during the X-ray fluoroscopy started in step ST3, that is, whether or not reception of a trigger signal from the trigger switch SW2 is started (step ST4).

If it is determined as "YES" in step ST4, that is, if it is determined that the reception of the trigger signal from the trigger switch SW2 is started, the first rotating function 71b determines whether or not the direction switch SW3 of the input interface 21 is tilted under a state where the trigger switch SW2 is pressed. That is, the first rotating function 71b determines whether reception of a direction signal from the direction switch SW3 is started during reception of the trigger signal from the trigger switch SW2 (step ST5). On the other hand, if it is determined as "NO", that is, if it is determined that reception of the trigger signal is not started, the first rotating function 71b waits until reception of the trigger signal from the trigger switch SW2 is started. It should be noted that the order of steps ST4 and ST5 may be reversed.

If it is determined as "YES" in step ST5, that is, if it is determined that reception of the direction signal is started during reception of the trigger signal, the rotational position recording function 71c receives the encoder signal from the C-arm rotating mechanism 41, calculates, based on the encoder signal, the rotational position of the C-arm 13, and records the rotational position in the memory circuit 72 (step ST6). On the other hand, if it is determined as "NO" in step ST5, that is, if it is determined that reception of the direction signal is not started during reception of the trigger signal, the first rotating function 71b waits until the reception of the direction signal is started.

If it is determined as "YES" in step ST5, that is, if it is determined that reception of the direction signal is started during reception of the trigger signal, the first rotating function 71b determines whether or not the mode set in step ST2 is the image reference mode (step ST7). If it is determined as "YES" in step ST7, that is, if it is determined that the mode set in step ST2 is the image reference mode, the first rotating function 71b sets the direction of the tilting operation of the direction switch SW3 as the moving direction of the imaging region of the displayed fluoroscopic images, and generates the first control signal so that the rotating direction of the C-arm 13 matches the moving direction (step ST8).

In the embodiment, in step ST8, the first rotating function 71b may display, on the display 64 (display unit 19), data indicating a relationship between a direction indicated by the direction signal and the rotating direction generated according to the direction. For example, when it is determined that the mode set in step ST2 is the image reference mode, the first rotating function 71b displays, in step ST8, image reference mode data indicating that the image reference mode is set, on the display 64, and informs the operator of the mode. As a result, the operator scheduled to operate the direction switch SW3 is able to operate the direction switch SW3, after recognizing, on the display 64, that the current state is the mode in which the direction of the tilting operation of the direction switch SW3 coincides with the moving direction of the imaging region of the displayed fluoroscopic image.

FIG. 11A is a diagram showing a display example of the image reference mode data.

When the image reference mode is set as the mode, the image reference mode data shown in FIG. 11A is displayed as an image on the display 64 together with the fluoroscopic image. For example, the image of the image reference mode data includes a model of the direction switch SW3, arrows of up, down, left and right directions of the direction switch SW3, and arrows around the fluoroscopic image corresponding to these arrows. With this display, the operator scheduled to operate the direction switch SW3 is able to recognize that the current state is the mode in which the direction of the tilting operation of the direction switch SW3 coincides with the moving direction of the imaging region of the displayed fluoroscopic image.

Returning to the explanation of FIG. 9, if it is determined as "NO" in step ST7, that is, if it is determined that the mode set in step ST2 is the arm reference mode, the first rotating function 71b generates the first control signal so that the direction of the tilting operation of the direction switch SW3 is the rotating direction of the C-arm 13 (step ST9).

In the embodiment, in step ST9, the first rotating function 71b may display, on the display 64 (display unit 19), data indicating a relationship between a direction indicated by the direction signal and the rotating direction generated according to the direction. For example, when it is determined that the mode set in step ST2 is the arm reference mode, the first rotating function 71b displays, in step ST9, arm reference mode data indicating that the arm reference mode is set, on the display 64, and informs the operator of the mode. As a result, the operator scheduled to operate the direction switch SW3 is able to operate the direction switch SW3, after recognizing, on the display 64, that the current state is the mode in which the direction of the tilting operation of the direction switch SW3 coincides with the rotating direction of the C-arm 13.

FIG. 11B is a diagram showing a display example of the arm reference mode data.

When the arm reference mode is set as the mode, the arm reference mode data shown in FIG. 11B is displayed as an image on the display 64 together with the fluoroscopic image. For example, the image of the arm reference mode data includes a model of the direction switch SW3, arrows of up, down, left and right directions of the direction switch SW3, and rotating directions (CRA, CAU, LAO, and RAO) of the C-arm 13 corresponding to these arrows. With this display, the operator scheduled to operate the direction switch SW3 is able to recognize that the current state is the mode in which the direction of the tilting operation of the direction switch SW3 coincides with the rotating direction of the C-arm 13.

Returning to the explanation of FIG. 9, the first rotating function 71b controls, based on the first control signal generated in step ST8 or ST9, the C-arm rotating mechanism 41, and controls the first rotation of the C-arm 13 (step ST10).

The first rotating function 71b determines whether or not the tilting operation of the direction switch SW3 of the input interface 21 is released under a state where the trigger switch SW2 is pressed. That is, the first rotating function 71b determines whether the reception of the direction signal from the direction switch SW3 started in step ST5 is finished during the reception of the trigger signal from the trigger switch SW2 (step ST11). If it is determined as "YES" in step ST11, that is, if it is determined that the reception of the direction signal is finished during reception of the trigger signal, the first rotating function 71b finishes the first rotation of the C-arm 13 started in step ST10 (step ST12). On the other hand, if it is determined as "NO" in step ST11, that is, if it is determined that the reception of the direction signal is not finished during reception of the trigger signal, the first rotating function 71b continues the first rotation until the reception of the direction signal is finished.

If it is determined as "YES" in step ST11, that is, if it is determined that the reception of the direction signal has finished during the reception of the trigger signal, the rotational position acquiring function 71d acquires the rotational position of the C-arm 13 stored in the memory circuit 72 in step ST6 (step ST13).

The second rotating function 71e receives the encoder signal from the C-arm rotating mechanism 41 during the reception of the trigger signal, and calculates, based on the encoder signal, the rotational position of the C-arm 13. Then, the second rotating function 71e generates, based on the calculated rotation position of the C-arm 13, the second control signal for returning to the rotational position of the C-arm 13 acquired in step ST13 (step ST14).

The second rotating function 71e controls, based on the second control signal generated in step ST14, the C-arm rotating mechanism 41, executes the second rotation of the C-arm 13, finishes the reception of the trigger signal started by "YES" in step ST4 (step ST15). That is, not only the control of stopping the first rotation of the C-arm 13 by releasing the tilting operation of the direction switch SW3, but also control to return the C-arm 13 to the previous rotational position is performed.

The X-ray imaging apparatus 1 determines whether the fluoroscopy end switch (not shown) of the input interface 21 has been pressed by the operator, that is, whether or not the X-ray fluoroscopy started in step ST3 is ended (step ST16). If it is determined as "YES" in step ST16, that is, if it is determined that X-ray fluoroscopy started in step ST1 is to be ended, the X-ray imaging apparatus 1 ends the X-ray fluoroscopy. It should be noted that the end of the X-ray fluoroscopy is not limited to the timing after step ST15. For example, the end of the X-ray fluoroscopy may be ended before the second rotation of the C-arm 13 is executed in step ST15.

On the other hand, if it is determined as "NO" in step ST16, that is, if it is determined that the X-ray fluoroscopy started in step ST3 is not to be ended, the first rotating function 71b determines whether the trigger signal from the trigger switch SW2 is received during X-ray fluoroscopy started in step ST3 (step ST4).

It should be noted that the rotational position recording function 71c updates and registers, by repeating a set of steps ST4 to ST16, the rotational position of the C-arm 13 in step ST6. The rotational position recording function 71c updates the rotational position of the C-arm 13, stored in the memory circuit 72 in the previous step ST6, to a new rotational position to be recorded in step ST6.

Steps ST1, ST2, ST7, and ST8 shown in FIG. 9 are not indispensable steps for the X-ray imaging apparatus 1. When there are no steps ST1, ST2, ST7, ST8 in the X-ray imaging apparatus 1, the X-ray imaging apparatus 1 may start X-ray fluoroscopy for the patient P (step ST3), may determine whether or not the reception of the trigger signal from the trigger switch SW2 is started (step ST4), may determine, when it is determined that reception of the trigger signal from the trigger switch SW2 is started, whether reception of the direction signal is started (step ST5), and may calculate the rotational position of the C-arm 13 and record it in the memory circuit 72 when it is determined that the reception of the direction signal is started during reception of the trigger signal (step ST6). Next, the X-ray imaging apparatus 1 generates the first control signal so that the direction of the tilting operation of the direction switch SW3 is the rotating direction of the C-arm 13 (step ST 9), and proceeds to step ST10.

According to the X-ray imaging apparatus 1, it is possible to automatically return to the previous rotational position after the first rotation of the C-arm 13 during the X-ray fluoroscopy, so that operability of the C-arm 13 by the operator such as a surgeon is improved. Further, according to the X-ray imaging apparatus 1, the direction of the tilting operation of the direction switch SW3 during X-ray fluoroscopy is set as the moving direction of the imaging region of the displayed fluoroscopic image, so that operability of the C-arm 13 by the operator is improved.

First Modified Example

In the flowcharts shown in FIGS. 9 and 10, the control has been described, the control being of continuing the reception of the trigger signal from "YES" in step ST11 to step ST15, and of continuing the second rotation of the C-arm 13 in the meantime. However, it is not limited to that case. For example, the processing circuitry 71 may control the C-arm 13 to finish the second rotation when the reception of the trigger signal is finished from "YES" in step ST11 to step ST15.

The operator is able to stop, with such control of the C-arm 13, the second rotation at an arbitrary rotational position while watching the fluoroscopic images during the second rotation of the C-arm 13. If it is desired to resume rotation of the C-arm 13 after stopping the second rotation, the operator presses the trigger switch SW2 (step ST4).

Second Modified Example

In step ST8 (or ST9) of the flowchart shown in FIG. 9, when the first rotating function 71b generates the first control signal, the first rotating function 71b may perform the position control of the table 14 so that the target part on the fluoroscopic image before the first rotation of the C-arm 13 appears at arbitrary positions on the fluoroscopic images during the first rotation.

FIG. 12A is a diagram showing a state of the C-arm provided in the X-ray imaging apparatus 1 before the first rotation. FIG. 12B is a diagram showing the fluoroscopic image displayed in the state shown in FIG. 12A. FIG. 13A is a diagram showing a state of the C-arm provided in the X-ray imaging apparatus 1 after the first rotation. FIG. 13B is a diagram showing the fluoroscopic image displayed in the state shown in FIG. 13A.

FIG. 12A shows a relationship between the X-ray tube 11a and the FPD 31 before the first rotation, an emitting region of the X-ray from the X-ray tube 11a, the target part R of the patient P placed on the table 14. With the emitting region of the X-ray shown in FIG. 12A, the target part R appears on the fluoroscopic image (FIG. 12B).

From the state shown in FIG. 12A, the first rotation of the C-arm around the isocenter "IS" is, while the position of the table 14 is fixed, performed. In other words, the first rotation is performed around the isocenter "IS" integrating the X-ray tube 11a and the FPD 31 (LAO in FIG. 13A). During the first rotation, the position of the target part R on each fluoroscopic image changes moment by moment. In some cases, as shown in the state after the first rotation shown in FIG. 13A, the target part R steps out of the emitting region of the X-ray (FIG. 13B). Therefore, it is necessary to control the position of the table 14 so that the target part R appears at an arbitrary position on each fluoroscopic image generated during the first rotation.

FIG. 14A is a diagram showing the fluoroscopic image displayed in a state of the C-arm provided in the X-ray imaging apparatus 1 before the first rotation. FIG. 14B is a diagram showing a two-dimensional position of the target part set by the fluoroscopic image or the like shown in FIG. 14A. FIG. 15A is a diagram showing a state, under the position control of the table, of the C-arm provided in the X-ray imaging apparatus 1 after the first rotation. FIG. 15B is a diagram showing the fluoroscopic image displayed in the state shown in FIG. 15A.

FIG. 14A shows the fluoroscopic image before the first rotation shown in FIG. 12B, and the position S set in the target part R on the fluoroscopic image. The operator specifies the position S in the target part R. The operator specifies the height of the position S before rotating the C-arm. That is, the operator specifies the height of the position S from the table 14.

FIG. 14B shows a position S' on the FPD 31 corresponding to the position S. The position S' is calculated based on the position set by FIG. 14A, the position of the C-arm 13, the position of the isocenter "IS", the source to image receptor distance (SID), the field of view FOV), the position of the table 14 and the like. FIG. 14B shows a three-dimensional position T [X, Y, Z] on the X-ray ray from the X-ray tube 11a to the position S' on the FPD 31 and on the height of the table 14, the three-dimensional position T [X, Y, Z] existing at a position to which the height of the set position S is added.

The first rotating function 71b generates, based on the three-dimensional position T before the first rotation, the control signal for performing sliding the table 14 such that the three-dimensional position T, that is, the target part R appears in the same region on each fluoroscopic image generated during the first rotation, and transmits the control signal to the mechanism control circuit 16. The same region includes the same position and its peripheral position.

The table sliding mechanism 42 controls, when the first rotating function 71b generates the control signal for the table 14 and transmits it to the mechanism control circuit 16, the position of the table 14 during the first rotation, it becomes the state shown in FIG. 15A. In the example shown in FIG. 15A, the table 14 is slid downward. In that case, the target part R (FIG. 12B) on the fluoroscopic image before the first rotation appears in the same region on each fluoroscopic image during the first rotation (FIG. 15B).

It should be noted that the position control of the table 14 during the first rotation of the C-arm 13 has been described with reference to FIGS. 14A and 14B and FIGS. 15A and 15B. In addition, it is also possible to control the position of the table 14 during the second rotation of the C-arm 13.

The operator is able to visually recognize, with such control of the table 14, the target part R within a fixed region on the fluoroscopic images during the first rotation (or the second rotation) of the C-arm 13.

Third Modified Example

In step ST8 (or ST9) of the flowchart shown in FIG. 9, when the first rotating function 71b generates the first control signal, the first rotating function 71b may perform the position control of the diaphragms of the X-ray beam limiter 11b, that is, the FOV control, so that the target part on the fluoroscopic image before the first rotation of the C-arm 13 appears at arbitrary positions on the fluoroscopic images during the first rotation. In combination with the control of the FOV, or in place of the control thereof, the first rotating function 71b may control the reading area of the FPD 31, that is, control the usage detecting element such that the target part on the fluoroscopic image before the first rotation of the C-arm 13 appears at an arbitrary position on each fluoroscopic image during the first rotation.

As described with reference to FIGS. 13A and 13B, during the first rotation, the position of the target part R on each fluoroscopic image changes moment by moment. Therefore, the first rotating function 71b calculates the three-dimensional position T [X, Y, Z], based on the position S set by FIG. 14A, the position of the C-arm 13, the position of the isocenter "IS", the SID, the FOV before change, the position of the table 14, and the like. The first rotating function 71b generates, based on the three-dimensional position T before the first rotation, the control signal for sliding each diaphragm of the X-ray beam limiter 11b such that the three-dimensional position T appears in the same region on each fluoroscopic image generated during the first rotation, and transmits the control signal to a diaphragm sliding mechanism (not shown). As a result, since the FOV is appropriately restricted during the first rotation, the target part on the fluoroscopic image before the first rotation of the C-arm 13 appears at an arbitrary position on each fluoroscopic image during the first rotation.

In combination with or in place of the control of the X-ray beam limiter 11b described above, the first rotating function 71b generates, based on the three-dimensional position T before the first rotation, a control signal for selecting a usage detection element from the X-ray detection elements included in the FPD such that the three-dimensional position T, that is, the target part R appears in the same region on each fluoroscopic image generated during the first rotation, and transmits the control signal to a switching circuit (not shown) for selecting the usage detecting element. Therefore, during the first rotation, the usage detection element is appropriately limited, and the target part on the fluoroscopic image before the first rotation of the C-arm 13 appears at the arbitrary position on each fluoroscopic image during the first rotation.

It should be noted that the control of the FOV during the first rotation of the C-arm 13 and the control of the usage first detecting element have been described. In addition, even during the second rotation of the C-arm 13, the FOV control and the usage detecting element control may be performed.

The operator is able to visually recognize, with such control of the FOV or the usage detecting element, the target part R within a fixed region on the fluoroscopic images during the first rotation (or the second rotation) of the C-arm 13.

Fourth Modified Example

In step ST6 shown in FIG. 9, the case where the rotational position recording function 71c receives the encoder signal and records the rotational position of the C-arm 13 after it is determined that the reception of the direction signal is started during reception of the trigger signal, has been described. However, the timing of recording the rotational position of the C-arm 13 is not limited to that case. For example, the rotational position recording function 71c may receive the encoder signal immediately after receiving the trigger signal or after receiving the trigger signal and before receiving the direction signal, and record the rotational position of the C-arm 13.

According to at least one embodiment described above, it is possible to improve operability of the arm by the operator.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An X-ray imaging apparatus, comprising:
an X-ray generator configured to generate X-rays;
an X-ray detector configured to detect the X-rays;
an arm configured to hold the X-ray generator and the X-ray detector;
an input interface configured to generate a direction signal for determining a rotating direction of the arm; and
processing circuitry configured to
display, on a display, an image based on the X-rays detected by the X-ray detector,
control, based on a first control signal according to the direction signal, a rotating mechanism of the arm so that the arm performs a first rotation, and
control, in response to an end of the first rotation, based on a second control signal, the rotating mechanism so that the arm performs a second rotation which returns the arm toward a position before the first rotation, the position being stored in a memory circuit, wherein
the processing circuitry is configured to perform the first rotation of the arm according to a user operation via the input interface, and automatically return the arm toward the position before the first rotation in response to the end of the first rotation, and
the input interface is configured to generate a mode signal indicating whether a current mode is an arm reference mode or an image reference mode, the arm reference mode being for setting the rotating direction as a direction indicated by the direction signal, and the image reference mode being for setting the rotating direction determined by setting a direction indicated by the direction signal as a moving direction of the image.

2. The X-ray imaging apparatus according to claim 1, wherein
the input interface includes a trigger switch configured to generate a trigger signal, and a direction switch configured to generate the direction signal, and
the processing circuitry is configured to control, when receiving the direction signal during reception of the trigger signal, the rotating mechanism so that the arm performs, based on the first control signal according to the direction signal, the first rotation.

3. The X-ray imaging apparatus according to claim 2, wherein
the processing circuitry configured to control, when the reception of the direction signal is finished during the first rotation of the arm, the rotating mechanism so that the arm finishes the first rotation and performs the second rotation.

4. The X-ray imaging apparatus according to claim 3, wherein
the processing circuitry is configured to control, when receiving the trigger signal during the second rotation of the arm, the rotating mechanism so that the arm finishes the second rotation.

5. The X-ray imaging apparatus according to claim 1, wherein
the processing circuitry is configured to record, based on the direction signal, the rotational position before the first rotation in the memory circuit.

6. The X-ray imaging apparatus according to claim 1, wherein
the processing circuitry is configured to display, on the display, data indicating a relationship between a direction indicated by the direction signal and the rotating direction generated according to the direction.

7. The X-ray imaging apparatus according to claim 1, wherein
the processing circuitry is configured to display, on the display, data indicating the image reference mode is set when the image reference mode is set.

8. The X-ray imaging apparatus according to claim 1, wherein
the processing circuitry is configured to display, on the display, data indicating the arm reference mode is set when the arm reference mode is set.

9. The X-ray imaging apparatus according to claim 1, wherein
the processing circuit is configured to
calculate a three-dimensional position of a target part, based on a position of the target part set on the image and a height of the target part from a table on which a subject is placed,
generate a control signal such that the target part appears in substantially a same region on images generated during the first rotation of the arm, based on the three-dimensional position, and
control sliding of the table during the first rotation of the arm, based on the generated control signal.

10. The X-ray imaging apparatus according to claim 1, wherein
the processing circuit is configured to
calculate a three-dimensional position of a target part, based on a position of the target part set on the image and a height of the target part from a table on which a subject is placed,
generate a control signal such that the target part appears in substantially a same region on images generated during the second rotation of the arm, based on the three-dimensional position, and control sliding of the table during the second rotation of the arm, based on the generated control signal.

11. The X-ray imaging apparatus according to claim 1, wherein
the processing circuit is configured to
calculate a three-dimensional position of a target part, based on a position of the target part set on the image and a height of the target part from a table on which a subject is placed,
generate a control signal such that the target part appears in substantially a same region on images generated during the first rotation of the arm, based on the three-dimensional position; and
control sliding of diaphragms of an X-ray beam limiter during the first rotation of the arm and/or control a reading area of the X-ray detector during the first rotation of the arm, based on the generated control signal.

12. The X-ray imaging apparatus according to claim 1, wherein
the processing circuit is configured to
calculate a three-dimensional position of a target part, based on a position of the target part set on the image and a height of the target part from a table on which a subject is placed,
generate a control signal such that the target part appears in substantially a same region on images generated during the second rotation of the arm, based on the three-dimensional position, and
control sliding of diaphragms of an X-ray beam limiter during the second rotation of the arm and/or control a reading area of the X-ray detector during the second rotation of the aim, based on the generated control signal.

13. The X-ray imaging apparatus according to claim 1, wherein
the processing circuit is configured to
calculate a three-dimensional position of a target part, based on a position of the target part set on the image and a height of the target part from a table on which a subject is placed,
generate a control signal such that the target part appears in within a fixed region within images generated during the first rotation of the arm, based on the three-dimensional position, and
control sliding of the table during the first rotation of the arm, based on the generated control signal.

14. An X-ray diagnostic apparatus, comprising:
an X-ray generator configured to generate X-rays;
an X-ray detector configured to detect the X-rays;
an arm configured to hold the X-ray generator and the X-ray detector;
an input interface configured to generate a direction signal for determining a rotating direction of the arm; and
processing circuitry configured to
display, on a display, an image based on the X-rays detected by the X-ray detector,
generate a control signal indicating a rotating direction of the arm, based on a mode signal indicating whether a mode is an arm reference mode or an image reference mode, the arm reference mode being for setting the rotating direction by setting the rotating direction as a direction indicated by the direction signal, and the image reference mode being for setting the rotating direction determined by setting a direction indicated by the direction signal as a moving direction of the displayed image, and
control a rotating mechanism of the arm so that the arm rotates, based on the control signal, wherein
the processing circuitry is configured to change a rotation direction of the arm depending on a mode selected from the two modes even though a same operation is performed by a user via the input interface.

15. An X-ray diagnostic apparatus, comprising:
an X-ray generator configured to generate X-rays;
an X-ray detector configured to detect the X-rays;
an arm configured to hold the X-ray generator and the X-ray detector;
an input interface configured to generate a direction signal for determining a rotating direction of the arm; and
processing circuitry configured to
display, on a display, an image based on the X-rays detected by the X-ray detector,
set a rotating direction determined by setting a direction indicated by the direction signal as a moving direction of the displayed image, thereby generating a control signal indicating the rotating direction of the arm, and
control a rotating mechanism of the arm so that the arm rotates, based on the control signal, wherein
the input interface is configured to generate a mode signal indicating whether a current mode is an arm reference mode or an image reference mode, the arm reference mode being for setting the rotating direction as a direction indicated by the direction signal, and the image reference mode being for setting the rotating direction determined by setting a direction indicated by the direction signal as a moving direction of the image.

16. The X-ray diagnostic apparatus according to claim 15, wherein the processing circuitry is configured to rotate the arm in a direction for realizing the moving direction of the displayed image according to a user operation via the input interface.

* * * * *